United States Patent [19]
Uhen et al.

[11] Patent Number: 5,983,710
[45] Date of Patent: Nov. 16, 1999

[54] MODULAR CHROMATOGRAPHY COLUMN HEATING SYSTEM

[75] Inventors: David A. Uhen, Burlington; Troy A. VerStrate, Oak Creek, both of Wis.

[73] Assignee: Brinkman Instruments, Inc., Westbury, N.Y.

[21] Appl. No.: 08/977,250

[22] Filed: Nov. 24, 1997

[51] Int. Cl.⁶ ................................................. G01N 30/54
[52] U.S. Cl. ........................................ 73/61.52; 73/23.25
[58] Field of Search ............................... 73/23.25, 61.52; 210/198.2, 656; 95/87

[56] References Cited

U.S. PATENT DOCUMENTS

| | | | |
|---|---|---|---|
| 4,044,593 | 8/1977 | Haruki et al. . | |
| 4,088,458 | 5/1978 | Jourdan | 96/102 |
| 4,311,900 | 1/1982 | Hummel | 219/535 |
| 4,350,586 | 9/1982 | Conlon et al. | 210/149 |
| 4,534,941 | 8/1985 | Stephens et al. . | |
| 4,966,695 | 10/1990 | Joshua | 210/198.2 |
| 5,215,556 | 6/1993 | Hiller et al. | 95/87 |

OTHER PUBLICATIONS

Supelco catalog p. 347, 1992, SSI Model 505 LC Column Oven.
The Anspec Company, Inc. Bulletin #17, p. 18, HPLC Temperature Control, published prior to 1997.
Brochure, Alltech Model 330 Column Heater, published prior to 1997.
Pickering Laboratories brochure, CHX650 Column Temperature Controllers, 1992.
Novex brochure, TSK–6097 Column Thermostat for HPLC, published prior to 1997.
Lab Products International, Dec. 1992, advertisement: Column Oven for HPLC/SFC.
Brochure (3 pages) entitled "HPLC Temperature Control Systems," Eppendorf, published prior to 1997.
Rainin Catalog—§ 5.01 Dynamax Model A1–1A Automatic Sample Injector, § 7.08 ICI.
Air Oven for Column Temperature Control, § 8.01 Timberline Instruments Low–Cost Column Temperature Controller, § 8.02 Timberline Instruments Stackable Front–Entry Column Heater, § 8.03 Eldex HDCL Column Temperature Controller, published prior to 1997.
Brochure page, Meta Therm Column Heaters, published prior to 1997.
Alltech brochure, pp. 10–11, Timberline Column Heaters, Reaction Module, and Controller, published prior to 1997.
Brochure by Jones Chromatography, New Model 7990 Space Column Heater, New Model 7955 HPLC Column Heater/Chiller, published prior to 1997.

(List continued on next page.)

*Primary Examiner*—Michael Brock
*Assistant Examiner*—Jay L. Politzer
*Attorney, Agent, or Firm*—Foley & Lardner

[57] ABSTRACT

A modular chromatography column heating and temperature control system includes a heater base module with a compartment for the chromatography column that includes a heater plate. A set of heater blocks is provided in pairs, each heater block having opposite main faces in which are formed channels that match chromatography columns of different diameters. The heater blocks are mounted in pairs on the heater plate with the chromatography column held between them in matching channels on the two adjacent main faces of the heater blocks. An appropriate number of pairs of heater blocks are mounted to the heater plate so that the pairs of heater blocks cover as much of the length of the chromatography column as desired. The set of available pairs of heater blocks may include heater blocks of different lengths, so that appropriate selections of pairs of heater blocks can be made to best match the length of the chromatography column. The heater blocks are formed of a good heat conductor, such as aluminum, to efficiently conduct heat from the heater plate to the chromatography column or away from the chromatography column to maintain the column at a desired temperature.

30 Claims, 5 Drawing Sheets

OTHER PUBLICATIONS

Euramark brochure, Mistral HPLC Column Thermostat, Full Range HPLC Temperature Control, published prior to 1997.

Brochure, JM Science, Inc., High Precision Column Oven for HPLC Heating and Cooling, Programmable Kuhlofen K–4 for HPLC, published prior to 1997.

Brochure, Bio–Rad HPLC Column Heater: High Control at a Low Price, 1992.

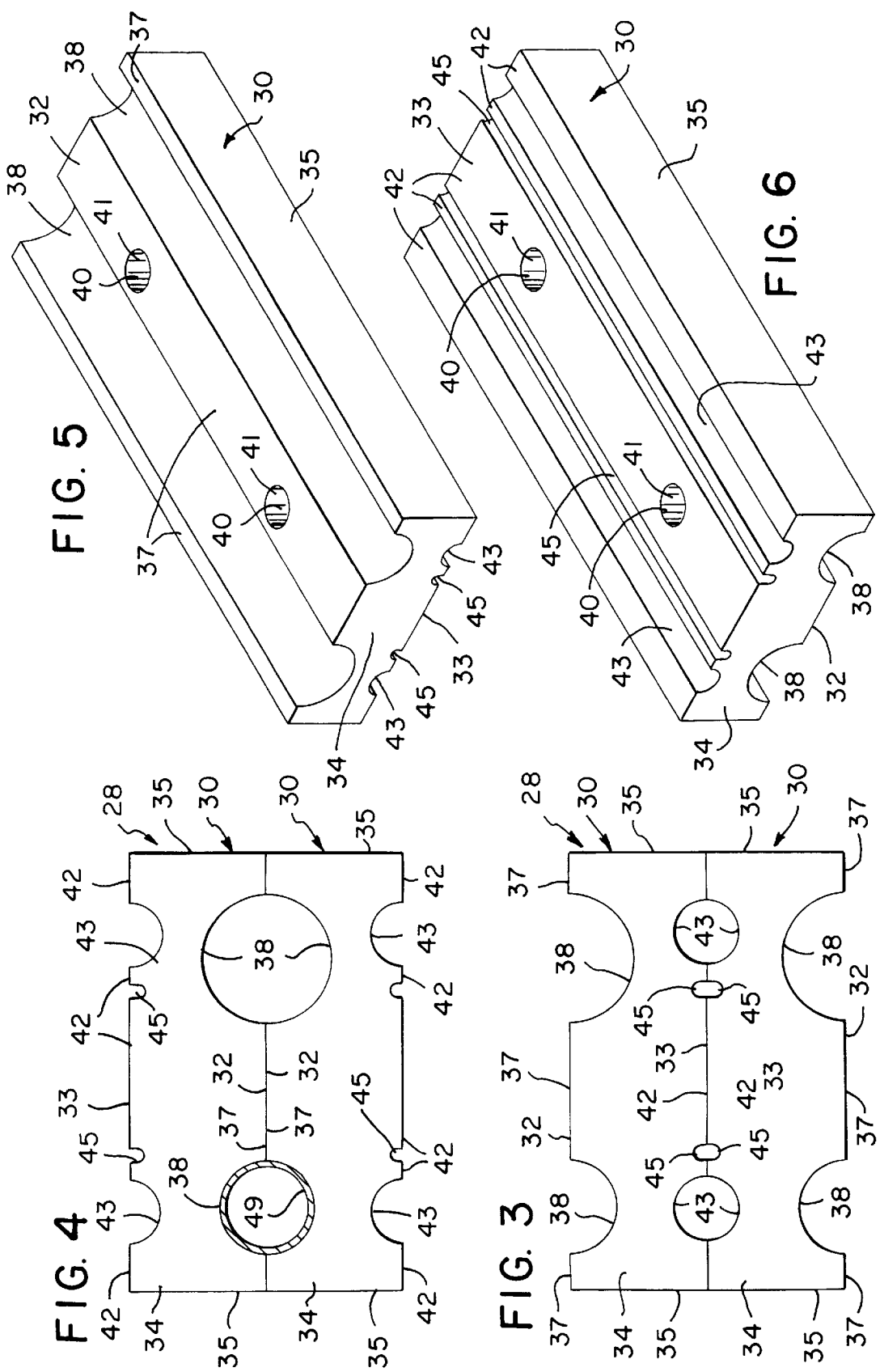

MODULAR CHROMATOGRAPHY COLUMN HEATING SYSTEM

FIELD OF THE INVENTION

This invention pertains generally to the field of instruments for chromatography such as high pressure liquid chromatography, and particularly to chromatography column heaters and temperature controllers.

BACKGROUND OF THE INVENTION

Chromatography is a process used in chemical and biochemical research and process control wherein mixtures of chemical compounds are separated into the components of the mixture so that the existence and quantity of each component can be determined. Chromatography is used, for example, in the pharmaceutical industries in basic research, product development, manufacturing, and quality control. In the high pressure (or performance) liquid chromatography (HPLC) process, a stainless steel tube, called a "column," is used to carry out the separation. Various materials can be used to fill the column, with a common filler bed material being $SiO_2$ (silicon dioxide or silica). A mobile phase liquid is then pushed through the column under pressure. Because the bed of material (e.g., silica) within the column is very dense, the liquid must be pressurized to a relatively high-pressure (e.g., 2,000–5,000 pounds per square inch) to force the liquid through the column at an acceptable rate. A sample constituting a mixture of chemical compounds to be analyzed is then introduced into the fluid stream and enters the column. As the chemical mixture passes through the bed within the column, the different chemicals in the mixture separate from one another depending on the partition coefficients of the various constituents.

The close control of the temperature of the column is essential to detector baseline stability and retention time reproducability. Without close control of the temperature of the column, typical daily ambient air temperature fluctuations of 3° to 4° C. are sufficient to cause erroneous quantitation or peak misidentification, particularly in automated systems or where temperature-sensitive detectors are used. In addition, it is often desirable to heat the column above ambient temperature. Elevated column temperatures can have the benefits of shorter analysis time, more reproducible results, greater sensitivity, co-eluting peak resolution, reduced mobile phase viscosity, less system wear and improved sample solubility. Thus, temperature controlled heaters for HPLC columns are in common use. Commonly, in such heaters the HPLC column is contained in an enclosure or "oven," the temperature of which is raised to a set temperature above ambient by an electrical heating element within the enclosure. Such column heater systems may also include a preheater to preheat the mobile phase before it reaches the column. Examples of designs for such preheaters include thin walled tubes carrying the mobile phase liquid which pass through heated metal blocks or which are wound around heated posts.

In some situations, the actual temperature within the column may not be adequately regulated by controlling the temperature of the ambient air around the column within the heater enclosure. To provide more precise direct control of the temperature of the column, the column may be mounted in contact with a block of good heat conducting metal (typically aluminium) which is itself in good thermal contact with the heating element of the column heather. The column may be mounted in a groove, typically V-shaped, in the conducting block to increase the heat transfer contact area between the outside surface of the column and the heat conducting block. The block of metal acts to transfer heat to or from portions of the column to rapidly equalize the temperature of all parts of the column in addition to transfer heat to or from the column as a whole to maintain the column at the desired temperature.

One limitation of conventional heaters using heat conducting blocks is that HPLC columns come in different lengths and in different outside diameters, ranging from relatively short columns of a few centimeters (cm) in length up to 60 cm and sometimes more. A heat conducting block of a length sufficient to be in contact with a long HPLC column over substantially its entire length cannot be used with a shorter column. Thus, several heat transfer blocks, each sized to fit a particular length of HPLC column, have been required. Such prior heat conducting blocks also generally only contact a portion of the outside periphery of the HPLC columns, so that the actual heat transfer area is much less than the full available surface of the column. Further, in conventional column heaters in which the preheaters are formed on posts mounted within the temperature controlled compartment, the space allocated in the compartment for the preheater structures can limit the maximum length of the HPLC column that can be used in conjunction with preheaters.

SUMMARY OF THE INVENTION

The modular chromatography column heating system of the present invention provides efficient and uniform temperature control of HPLC and similar chromatography columns of various lengths and diameters. The accommodation of the heating system to a different column is accomplished simply and easily by an operator without the need for special tools or for specialized heat transfer blocks matched in size to each size chromatography column. Preheater tubes for preheating the mobile phase liquid can be incorporated in the heated compartment along with the chromatography columns without requiring separate space for the preheaters within the compartment, thereby allowing use of preheaters with chromatography columns of the maximum length that can fit within the compartment.

The chromatography column heating system of the invention includes a compartment in which one or more chromatography columns may be mounted, a heater plate within the compartment, and pairs of mating heater blocks mounted within the compartment with one block of each pair supported by the heater plate. Each of the heater blocks is formed of a solid body of a good heat conducting metal. Each block has opposite main faces with flat reference surfaces on each, and opposite end faces which define the longitudinal ends of the heater blocks and which intersect with the main faces. At least one channel is formed in the main faces extending longitudinally between the end faces. The channels in each pair of blocks are formed to match with each other and to closely engage the external periphery of a tubular chromatography column when the column is engaged between the heater blocks. Pairs of heater blocks engaged together over the column are then secured to the underlying heater plate, for example, by a hand-turned screw which passes through matching attachment holes in the top and bottom heater blocks and threads into a threaded opening in the heater plate, or, preferably, into threaded standoffs mounted in the heater plate. The standoffs extend above the surface of the heater plate and fit into counter bores formed about the attachment holes in the heater blocks thereby also serving to quickly locate the blocks at their proper positions on the heater plate. The close engagement of the channels in the heater blocks with the outside periphery of the column results in rapid heat transfer between the column and the blocks, either to or from the column, over the entire circumference of the column rather than only a fraction of the circumference. Preferably, the channels in the heater blocks are half-cylindrical and closely matched in diameter to the outside diameter of the cylindrical chromatography column to provide heat transfer contact between the heater blocks and the chromatography column over substantially the entire periphery of the column.

To accommodate chromatography columns of different lengths in accordance with the invention, a set of pairs of heater blocks may be provided which, when engaged together, extend over a substantial portion of the compartment so as to be able to engage the longest chromatography column that can otherwise fit within the compartment. The set of pairs includes plural pairs of different lengths; for example, to accommodate columns of different lengths, the set of pairs may include one pair of maximum length (e.g., 4 inches), and a second pair of a shorter length (e.g., 2 inches). The set may include multiple pairs of the same length, e.g., two pairs of 4-inch length and/or two pairs of 2-inch length, and one or more pairs of other lengths, e.g., 1-inch. All of the pairs in the set may be mounted together on the heater plate with the end faces of the adjoining pairs in contact to define a continuous channel through the set within which may be mounted the chromatography column of greatest length. Where a chromatography column of lesser length is utilized, the operator may select a subset of the pairs of heater blocks which, when placed together with adjoining end faces in contact, most closely matches the length of the column (e.g., a subset of two 4-inch pairs and one 2-inch pair, a subset of one 4-inch pair and one 2-inch pair, a subset of one 4-inch pair, and a subset of a single 2-inch pair). To match the heater blocks to the length of a new chromatography column, the operator simply unscrews the screws which hold the blocks in place, lays down a set of bottom blocks of lengths which together best match the length of the chromatography column, engaging the heater blocks to the standoffs to locate the blocks in place on the heater plate with the channels in the bottom blocks aligned with one another, then sets the chromatography column into the channel formed in the aligned blocks and places the mating top blocks over the bottom blocks with the channels in the top blocks aligned with and engaging the top of the chromatography column. The pairs of blocks are then secured in place by reinserting the screws through the holes in the pairs of blocks and threading the screws into the threaded holes in the standoffs mounted in the underlying heater plate.

Further, in accordance with the invention, to accommodate chromatography columns of different diameters as well as different lengths, the pairs of heater blocks preferably have at least one channel formed in each of the main faces, with a channel in one of the main faces having a different width than a channel in the other main face. Each of the heater blocks is formed to have similar channels of the same width, the same spacing of the channels from the side faces and each other, and the same spacing of attachment holes from the faces. Thus, to accommodate a new chromatography column of a different diameter, the heater blocks may be removed by the operator and turned over so that the bottom block now has the channel with the proper width to match the chromatography column facing upwardly. Heater blocks of the desired length are then placed together with their end faces in contact to define a continuous channel of the proper width into which the new chromatography column may be placed, whereafter the upper heater blocks in each pair are mounted in place with the channel of proper diameter to match the chromatography column then engaged with the chromatography column. The pairs of heater blocks are then secured in place as before by passing the attachment screw through the attachment holes in the heater blocks and into the underlying tapped holes in the standoffs mounted in the heater plate. Preferably, each heater block has at least two channels formed in each main face. The channels may have various widths and combinations of widths as desired. For example, the two channels in a first main face may have the same width, whereas the two channels in the opposite main face may have different widths, both of which differ from the width of the two channels in the first main face. In this way, the heater blocks may be properly oriented in pairs together such that the widths of the channels in the main faces that adjoin each other in each pair match.

Each of the heater blocks also may include one, and preferably two or more, additional preheater channels of smaller width that are sized to admit and engage inlet tubing carrying the mobile phase liquid to transmit heat to this tubing from the heater blocks and thus preheat the mobile phase. Preferably, the preheat channels are formed in at least one of the main faces of the heater block to match and mate with preheater channels formed in a main face of another heater block. Preferably, the preheater channels meet at positions such that the other channels in the adjoining faces of the two blocks will also match each other. Two preheater channels may be formed in a main face which has two chromatography channels of different sizes, with the two preheater channels being equally spaced from the center line of the main face so that the preheater channels will meet with and match each other on the adjoining faces. The preheater channels may also be formed to be deeper than wide so that the preheater channels can hold the preheater tubing within the channels when the main face in which the channels are formed is mounted flat against the heater plate. By utilizing the preheater channels within the heater blocks to contain the preheater tubing, and thus preheat the moving phase, the need for separate heater posts or other preheaters within the heater compartment at the ends of the chromatography column is eliminated, thereby maximizing the space within the compartment of the heating system that can be utilized for holding the chromatography column.

The attachment holes in the heater blocks through which the attachments screw passes are preferably formed so that the center line of each hole is at a distance from the nearest end face that is one-half of the distance between the threaded holes in the standoffs in the heater plate. Thus, when two pairs of heater blocks are mounted to the heater plate with their end faces in contact, the spacing between the attachment holes in two adjoining pairs of heater blocks is equal to the spacing between the threaded holes in the standoffs on the underlying heater plate. Preferably, a linearly aligned series of such equally spaced standoffs with threaded holes is in the heater plate. The lengths of the heater blocks between their end faces is chosen so that the length of each block is preferably an integral multiple of the spacing between the center lines of the threaded holes in the heater plate standoffs. Where the length of a heater block is greater than the spacing between two holes (e.g., two or more times the spacing), two (or more) attachment holes may be formed in the heater blocks at proper spacings to align with the underlying holes in the heater plate. Heater blocks may also be formed having a length less than the spacing between the holes in the heater plate where shorter stand-alone blocks are needed, with the attachment hole passing through the center of the short heater blocks. Alternatively, other means may be used to hold the heater blocks in place, such as clamps extending up from the heater plate, mating tabs in the heater plate and holes in the heater blocks, and so forth. The use of hand turned attachment screws which pass through the blocks into the standoffs or the heater plate itself is preferred for ease of assembly and disassembly by an operator. Such screws allow secure attachment of the heater blocks to the heater plate and tight engagement of the blocks with the chromatography columns.

Further objects, features and advantages of the invention will be apparent from the following detailed description when taken in conjunction with the accompanying drawings.

BRIEF DESCRIPTION OF THE DRAWINGS

In the drawings:

FIG. 3 is an end view of the mated pair of heater blocks of FIG. 2.

FIG. 4 is an end view of the pair of heater blocks of FIGS. 2–3 with interchange of the main faces of the heater blocks that are in abutting relationship.

FIG. 5 is a perspective view illustrating one main face of a heater block in accordance with the invention.

FIG. 6 is a perspective view illustrating the other main face of the heater block of FIG. 5.

DETAILED DESCRIPTION OF THE INVENTION

Figure 1:
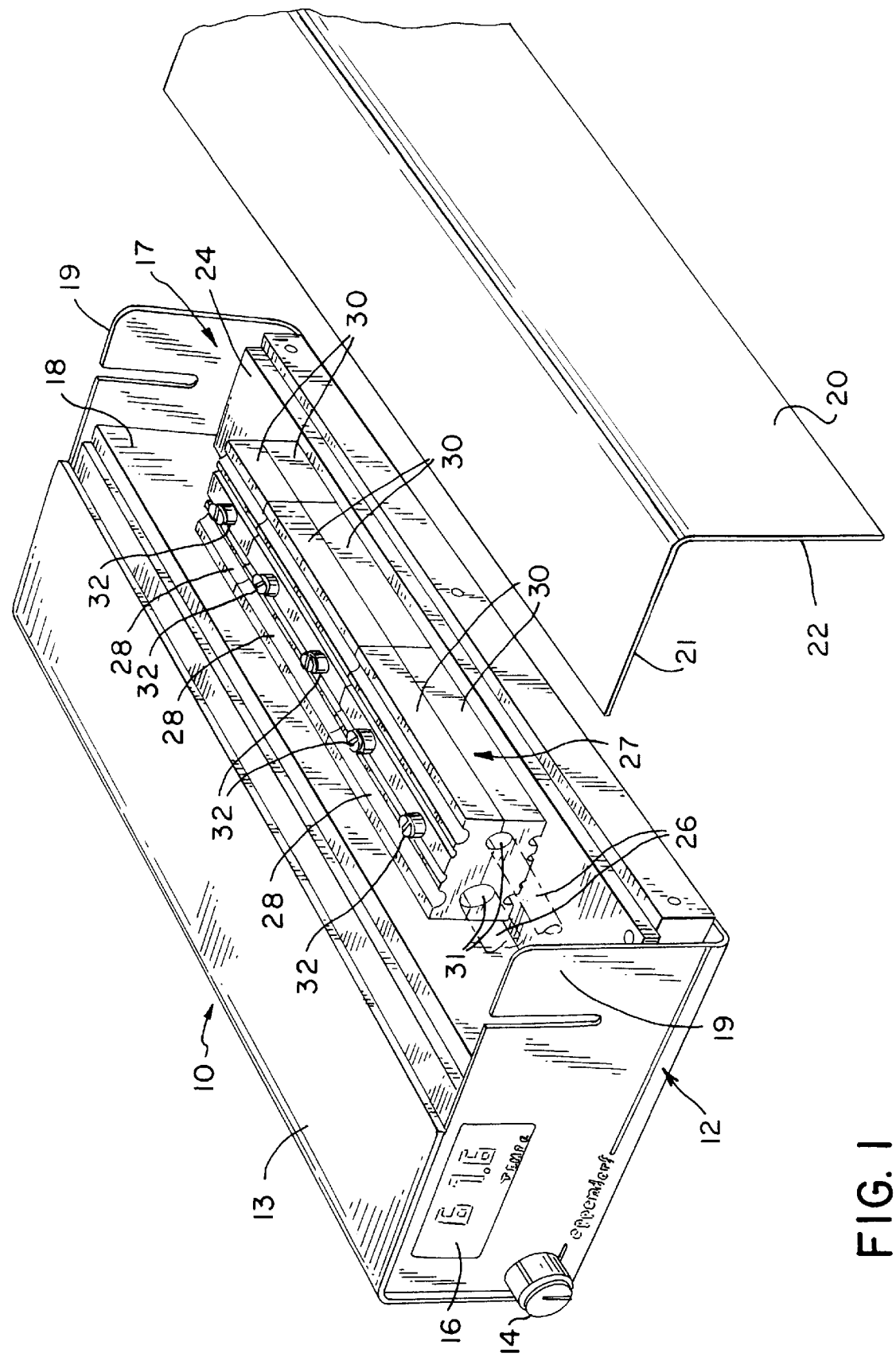
FIG. 1 is a perspective view of a chromatography column heater system in accordance with the invention illustrating a set of heater blocks mounted in place in a heater compartment.

With reference to the drawings, a perspective view of a modular chromatography column heater system in accordance with the invention is shown generally at 10 in FIG. 1. The system 10 includes a heater base module 12 of substantially conventional construction which includes heater power supplies and controllers within a cabinet enclosure 13. A control knob 14 allows the operator to select the temperature at which the heater will maintain the chromatography column, with the selected temperature displayed on a display device 16 (e.g., a light emitting diode (LED) display panel). The heater base module 12 includes a heater compartment 17 formed of enclosure walls, including a back wall 18, two side walls 19, and a removable panel 20 which defines a top wall 21 and an outer side wall 22. Although it is preferable that the compartment completely enclose the chromatography column to separate it from ambient atmosphere, an open compartment may be used if desired. Panels of insulation (not shown) may be mounted on the interior walls of the heater compartment 17 to further insulate the compartment from ambient atmosphere, if desired. The bottom of the compartment 17 is defined by a heater plate 24, the temperature of which is controlled by the control unit 13 supplying electrical power to an electrical heating element (not shown in FIG. 1) in a conventional manner to maintain the desired temperature within the compartment 17.

The foregoing heater base module 12 is of conventional construction and any suitable column heater base module may be utilized. Examples of suitable heater controllers are HPLC temperature control systems available from Eppendorf Scientific, Inc., Madison, Wis. The particular design or construction of the heater base module and the temperature controller are not critical to the present invention. The only requirement for such heating control systems is that they control the temperature of a heater plate 24 to a desired set temperature.

In accordance with the present invention, transfer of heat to and from the chromatography column(s), illustrated by the dashed lines 26 in FIG. 1, is mediated by a set 27 of heat conducting heater blocks which are in contact with the outer surface of the chromatography columns 26 and with the heater plate 24. The set 27 includes one or more pairs 28 of mating heater blocks 30. The pairs 28 of heater blocks are secured in place to the heater plate 24 by means of connectors 32, preferably hand-turned attachment screws which thread into threaded openings in standoffs (not shown in FIG. 1) in the heater plate 24, as explained further below. The chromatography column or columns 26 are held within the set 27 within cylindrical channels 31 defined by the mating pairs of blocks 30. The manner of connection of the chromatography columns 26 to the supply of the moving phase liquid and to the sample are conventional and are not shown in FIG. 1.

Figure 2:
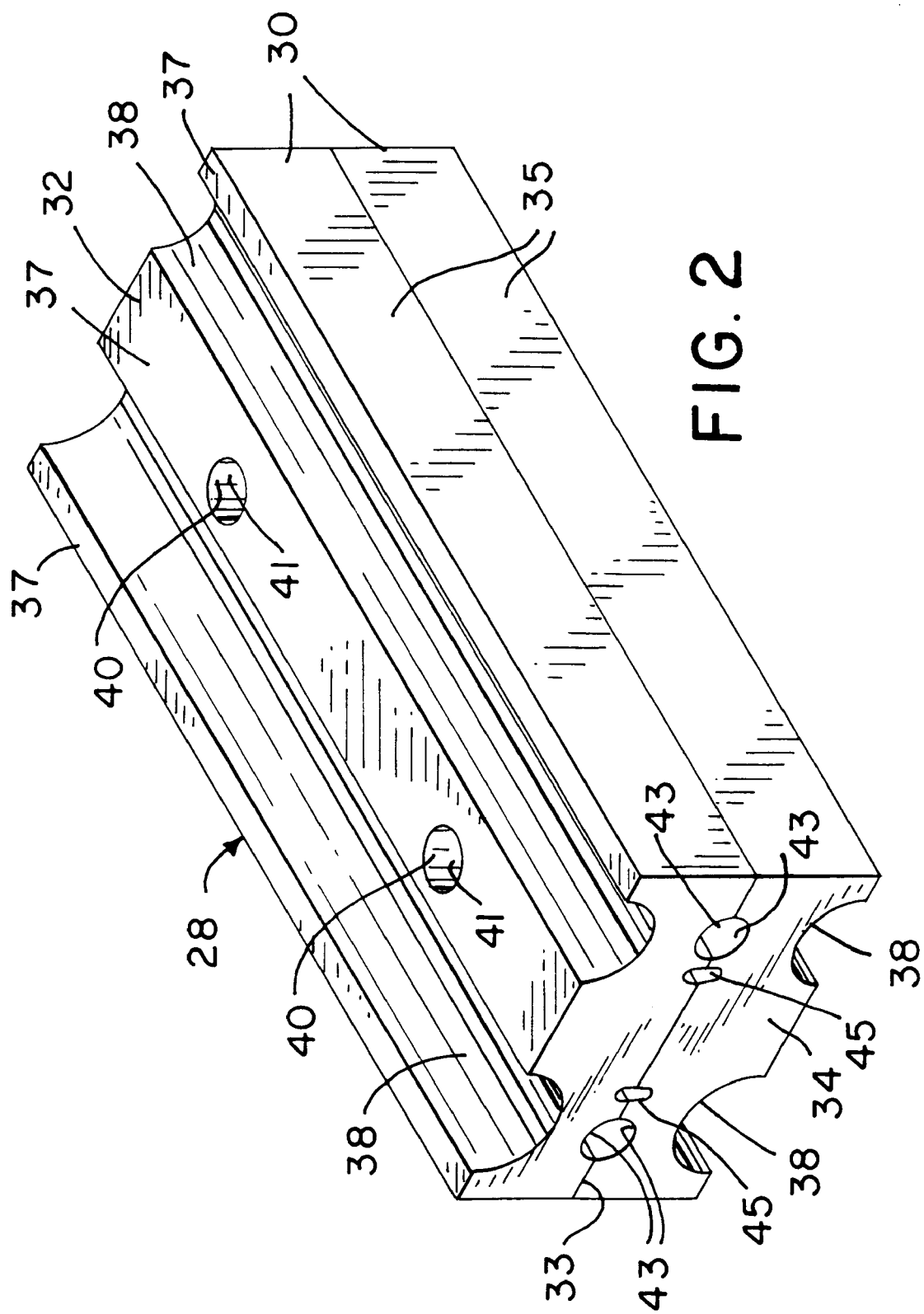
FIG. 2 is a perspective view of an exemplary mated pair of heater blocks in accordance with the invention.
Figure 9:
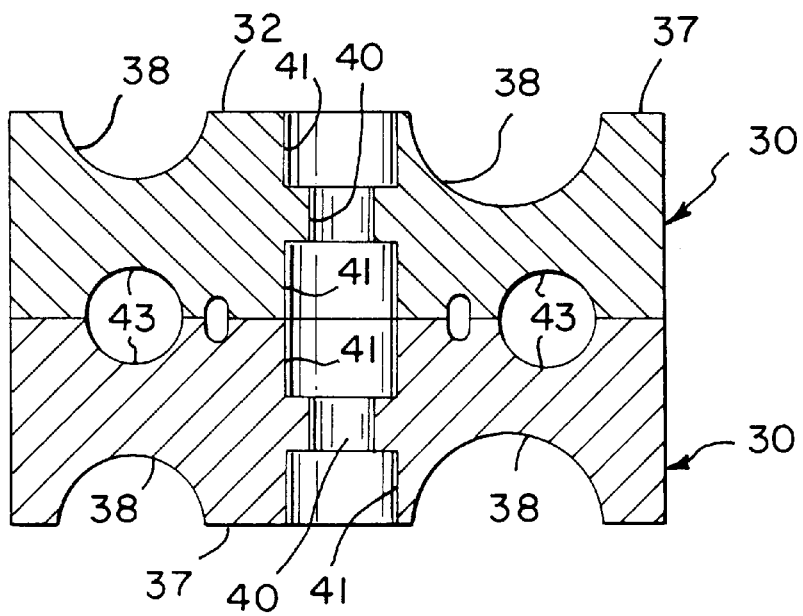
FIG. 9 is a cross-sectional view through a pair of heater blocks.

A pair 28 of the heater blocks 30 is shown in FIG. 2 in perspective, and the same pair is shown in an end view in FIG. 3. Each of the heater blocks 30 is identical in construction, preferably being formed of a solid body of a good heat conducting metal, such as extruded aluminum alloy (e.g., #6063-T5 aluminum alloy), which has high thermal conductivity, relatively low mass, and which quickly heats and cools. The body of each of the heater blocks 30 has two opposite main faces 32 and 33, flat end faces 34, and preferably flat side faces 35. In the arrangement of the pair of heater blocks 30 shown in FIGS. 2 and 3, the main faces 33 of each of the pair of blocks 30 are in abutting relationship, and the main faces 32 are facing outwardly. In the arrangement shown in side view in FIG. 4, the positions of the main faces of the blocks are interchanged, with the main faces 32 now abutting each other and the main faces 33 of each block 30 facing outwardly. Each main face 32 has flat, coplanar reference surfaces 37 and at least one longitudinally extending channel or channels 38 formed therein. Preferably, there are two channels 38, each formed as a half-cylindrical depression, and each having a different width (diameter, for a half-cylindrical depression) which corresponds to (and is slightly larger than) the diameters of chromatography columns in common use, e.g., 0.51-inch width (for a ½-inch diameter chromatography column) and 0.384-inch width (for a ⅜-inch diameter chromatography column). Each of the channels 38 extends longitudinally through the block 30 in a direction perpendicular to the end faces 34 of each block. An attachment hole (or holes) 40 is formed in each block 30 and extends between the main faces 32 and 33, preferably aligned in a direction which is perpendicular to the reference surfaces 37. As best illustrated in FIG. 9, each attachment hole 40 has a widened counter bore 41, of greater diameter than the rest of the hole 40, formed partially through the block about the hole 40 at each main face 32 and 33.

The main face 33, which is opposite and parallel to the main face 32, also has flat, coplanar reference surfaces 42, and at least one and preferably two longitudinally extending channels 43 formed therein. The channels 43 preferably are half-cylindrical, having a width which differs from the width of either of the channels 38 formed in the first main face 32. For example, the channels 43 may each have a width (a diameter of a half-cylindrical channel) of one-quarter inch (preferably slightly larger, e.g., 0.26 inch diameter) to best fit a quarter-inch diameter chromatography column. Although the two channels 43 can have different widths, it is preferred that the two channels 43 have the same width to thereby allow two separate columns or both a supply and return chromatography column to be temperature controlled at the same time. The main face 33 also preferably includes at least one and preferably two additional channels 45 which have a width sized to accept the typical thin preheater inlet tubing to the HPLC columns, e.g., a width of 0.070 inch for the channels 45. The channels 45 are preferably U-shaped in cross-section as shown, having a depth as great as width (e.g., 0.070 inch) so that conventional inlet tubing can be entirely contained within the channels 45 within a single block 30. Alternatively, the tubing can be run through the space defined by the mating channels 45 when the main faces 33 are placed in abutting relationship, as illustrated in FIGS. 2 and 3. FIG. 4 illustrates in cross section the cylindrical wall 49 of a chromatography column that is held within the facing channels 38 of the two heater blocks 30 when the main faces 32 of the heater blocks are placed in abutting relationship.

As is apparent from the side views of FIGS. 3 and 4, in either orientation of the blocks 30 (i.e., main faces 32 abutting or main faces 33 abutting), the respective channels in the main faces match with each other and the respective reference surfaces 37 and 42 are in contact with each other. Because the reference surfaces 37 or 42 are in contact with each other, good heat transfer occurs between the blocks 30 across these surfaces, either to transfer heat to or from chromatography columns held within the channels 38 or 43 or to preheat inlet tubing held within the channels 45. Similarly, the flat reference surfaces 37 or 42 make firm large area contact with the flat heater plate 24 to either transfer heat from the heater plate 24 to the blocks 30 or from the blocks 30 to the heater plate 24. The large exposed surface area of the blocks 30 (including the additional surface area in the main faces provided by the outwardly facing channels 38 or 43 as well as the end faces 34 and side faces 35), provides rapid transfer of heat from the blocks 30 to the ambient air in situations where the temperature of the chromatography columns is to be lowered and where the ambient air within the compartment 17 is at a temperature lower than that of the chromatography column(s).

In the foregoing manner, it is seen that the set 27 of heater blocks 30 can accommodate chromatography columns of different diameters simply by unscrewing the attachment screws 32 that hold the blocks in place, turning the blocks to a position in which the channels 38 or 43 of the desired size face and match with each other, laying the blocks on the heater plate 24 with the standoffs 50 inserted into the counter bores 41 of the blocks, and engaging the upper blocks in each pair over the chromatography column. The pairs of blocks are then secured in place by engaging the attachment screws 42 through the blocks 30 to the threaded holes in the standoffs 50 on the heater plate 24.

It is also a particular advantage of the present invention that the set 27 of pairs 28 of heater blocks 30 can be arranged to best fit the length of a chromatography column as well as the diameter of the column, thus allowing chromatography columns of various lengths to be utilized with the modular chromatography heater system 10 of the invention. As shown in FIG. 1, several pairs 28 of heater blocks may be utilized, and the blocks may have different lengths (i.e., the length of the block is the distance between its end faces 34). For example, the heater blocks 30 may include blocks in lengths of 4 inches (about 10 cm) and 2 inches (about 5 cm), and preferably also including a heater block of 1 inch (about 2.5 cm) length. Utilizing these three lengths for the blocks, the blocks 30 may be mounted together in pairs 28 with their end faces 34 in abutting relationship in the proper combination to best match a particular length of chromatography column. With the exemplary lengths for blocks listed above, exemplary total lengths for combinations of blocks include: 2 inches (one 2-inch block), 4 inches (one 4-inch block), 6 inches (one 4-inch block and one 2-inch block), 8 inches (two 4-inch blocks), and 10 inches (two 4-inch blocks and one 2-inch block). The one inch block may be used as needed either by itself over a short column or with other pairs of blocks (e.g., to best cover a column having a length slightly less than the length of the combinations listed above. As an example, the full set of pairs of blocks that may be accommodated within the compartment 17 may comprise two pairs of 4-inch blocks and two pairs of 2-inch blocks, with one 1-inch block pair being provided as a optional part.

Figure 7:
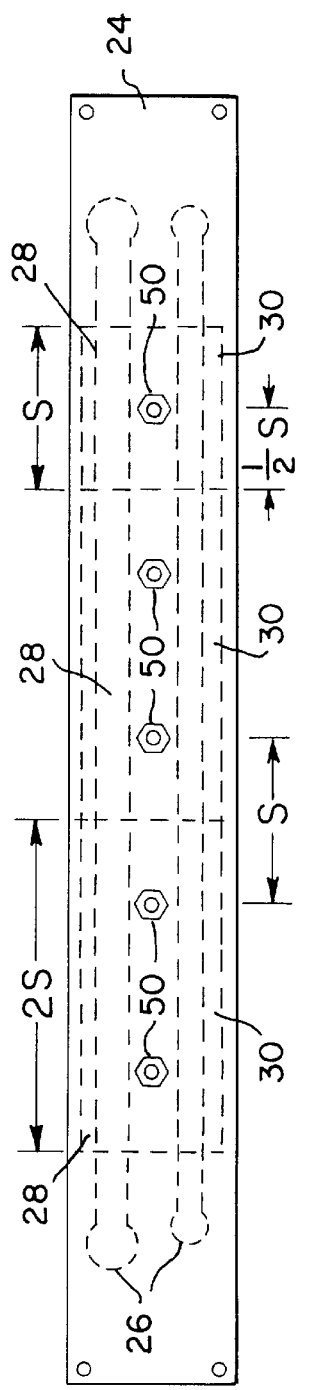
FIG. 7 is a top view of the heater plate of the system of FIG. 1 illustrating the position of the standoffs with threaded holes mounted in the heater plate.

As shown in FIG. 7, the heater plate 24 has a series of the standoffs 50 in linearly aligned evenly spaced relation, with threaded blind holes 51 formed in each standoff 50 to accept the attachment screws 32, which can be threaded into the standoffs 50 to secure the pairs of blocks 30 to the heater plate 24. Alternatively, threaded holes may be formed in similar spaced relation directly in the heater plate. The center lines of the standoffs 50 (and of the threaded holes therein) are spaced from each other a distance "S" (for example, S may be 2 inches). The attachment holes 40 in the heater blocks 30 are then formed at positions wherein their center lines are spaced one-half S from the end faces 34. Where the length of the heater block between the end faces 34 is greater than S, two (or more) holes 40 are formed in the blocks (as shown in FIG. 2), with the spacing between the center lines of the holes 40 equal to S. The length of the blocks will then be equal to integer multiples of S (e.g., where S equals 2 inches, the lengths of the blocks 30 would be 2 inches, 4 inches, and so forth). In this manner, when the desired number of pairs of the blocks 30 are set in place on the heater plate 24, the attachment holes 40 in the blocks can be aligned with the underlying tapped holes 51 in the standoffs 50 on the heater plate 24 so that the attachment screws 32 can be passed through the holes 40 into the tapped holes in the standoffs 50, as illustrated in FIG. 7, to secure the heater blocks into place in proper alignment and, where multiple pairs of blocks are used, to ensure that the pairs of blocks have their end faces closely approaching or abutting and that the channels in each adjoining pair of blocks line up so that a chromatography column can be properly inserted therein. As noted above, a shorter pair of blocks can be used, e.g., a 1-inch block where S is 2 inches. The 1-inch block can then be mounted in place engaging a short column by locating the counter bore 41 of the attachment hole 40 onto a standoff 50 and securing two of the short blocks together over a portion of a column. The short blocks are also secured by inserting an attachment screw through the hole 40 into the threaded hole 51 of the standoff 50 in the underlying heater plate.

In the foregoing manner, the number of pairs of blocks can be selected to cover as much as possible of the length of a particular chromatography column, thereby assuring good heat transfer to and from the chromatography column through the heat transfer blocks 30. Because the blocks 30 are in contact with the entire periphery of the chromatography column, and are in good heat transfer contact with each other and with the underlying heater plate 24, by controlling the temperature of the heater plate 24 good control can be maintained of the temperature of the chromatography column itself over substantially all of the length of the column.

Figure 8:
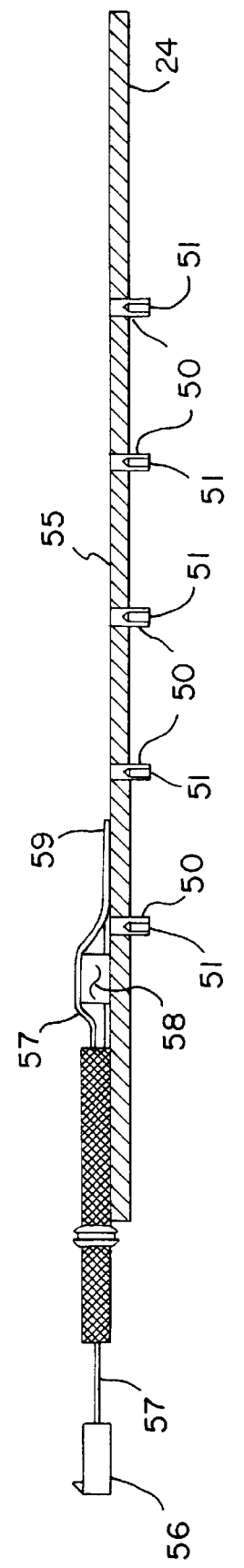
FIG. 8 is a partial cross-sectional side view of the heater plate of FIG. 7.

As illustrated with reference to FIG. 8, the heater plate 24 may be heated directly by a thermofoil resistance heater 55 which is adhered to the back side of the heater plate. The resistance heater 55 is supplied with electrical power through a connector plug 56 and supply wires 57. A thermostat 58 is mounted to the back of the heater plate, as is a thin film resistance temperature detector 59 which serves as a temperature sensor. The temperature sensor 59 is connected by wires to the connector plug 56 to allow control circuitry with the base unit 13 to monitor the temperature of the heater plate 24 and control the supply of power to the resistance heater 55. The thermostat 58 is connected in the power supply lines to the heater 55 to cut off power at a maximum operating temperature (e.g., 160° C.). The thermofoil heater 55 may cover substantially the entire back of the heater plate, including the bottoms of the standoffs 50, since the attachment screws 32 thread into blind holes in the standoffs and thus cannot penetrate the thermofoil heater. Alternatively, the attachment screws may engage directly with threaded holes 51 formed in the heater plate itself without use of the standoffs 50, but if such holes 51 extend through the heater plate the thermofoil heater 55 should be opened at the holes so that contact is not made between the attachment screws and the thermofoil heater.

The heat transfer blocks are preferably made of a good heat conducting metal, e.g., extruded aluminium as noted above, although other metals may be used, such as copper, etc. To enhance corrosion resistance, the surfaces of the heater blocks 30 may be appropriately coated, e.g., with an epoxy coating.

Figure 10:
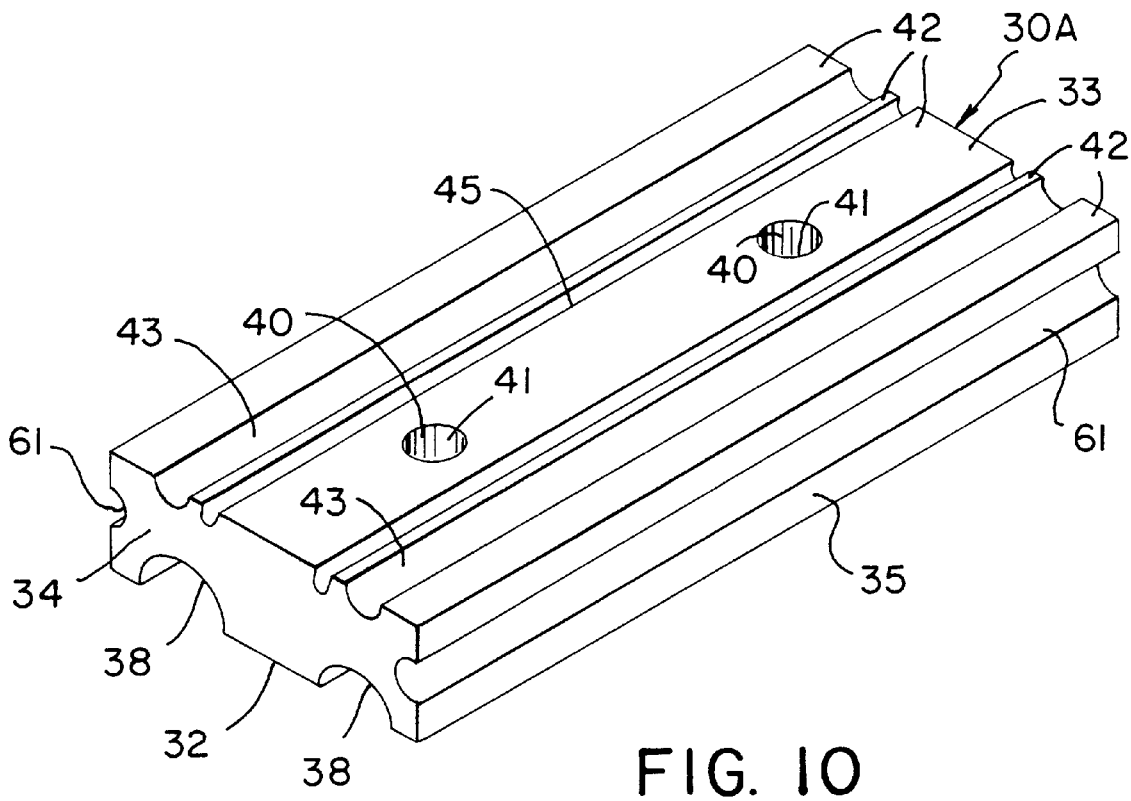
FIG. 10 is a perspective view of a modified heater block in accordance with the invention.

Although the use of pairs of vertically stacked heat transfer blocks is preferred, the blocks may also be formed for stacking horizontally. FIG. 10 illustrates a heater block 30A which is identical to the heater blocks 30 described above except that a longitudinal channel 61 is formed in each side face 35, the diameters of which are selected to match the diameters of standard chromatography columns. Two of the blocks 30A may thus be mounted with the side faces 35 in abutment with a column engaged between them in the channels 61. The side faces 35 may then be considered to function as main faces hereunder, which are in abutting relationship holding a column between them, when the pair of blocks 30A are mounted side by side on the heater plate.

It is understood that the invention is not confined to the particular embodiments set forth herein as illustrative, but embraces all such modified forms thereof as come within the scope of the following claims.

What is claimed is:

1. A heater block for use in a modular chromatography column heating system comprising:

a solid body of a good heat conducting metal, the body having two opposite main faces, each main face having flat, coplanar reference surfaces, the reference surfaces of each main face being parallel to the reference surfaces of the opposite main face, the body also having side faces and end faces, at least one longitudinal half-cylindrical channel for a chromatography column formed in each main face extending the length of the body between the end faces, the channels in the opposite main faces having different widths, and an attachment hole formed through the body between the main faces.

2. The heater block of claim 1 wherein at least two channels are formed in each main face that extend between the end faces parallel to each other.

3. The heater block of claim 2 wherein two additional parallel channels for preheater tubes are formed in one of the main faces parallel to the other channels in the main face and extending the length of the heater block between the end faces, the two additional channels having a width smaller than the width of the half-cylindrical channels in the main face.

4. The heater block of claim 1 wherein the body of the heater block is formed of aluminum and including a corrosion resistant coating on the surfaces of the body.

5. The heater block of claim 1 wherein the end faces of the heater block are flat and parallel to each other, the channels in the main faces are formed perpendicular to the end faces, and wherein the length of the heater block between the end faces is an even integer multiple of the distance between a center line of the attachment hole through the heater block body and the most closely adjacent end face.

6. The heater block of claim 1 wherein the side faces of the heater block are parallel to each other and parallel to the channels formed in the main faces, wherein one of the main faces has two half-cylindrical channels formed therein of the same width and wherein such channels are parallel to and spaced an equal distance from the side faces.

7. The heater block of claim 1 further including a longitudinal half-cylindrical channel formed in each side face between the end faces.

8. The heater block of claim 1 wherein one of the main faces has two half-cylindrical channels formed therein which are about ¼ inch in width, the other main face has two half-cylindrical channels formed therein, one of which is about ½ inch in width and the other of which is about ⅜ inch in width.

9. The heater block of claim 8 wherein one of the main faces has two additional channels formed therein between the end faces to accommodate preheater tubes therein, each additional channel having a width of about 0.070 inch.

10. The heater block of claim 1 further including a counter bore that is wider than the attachment hole formed in the body about the attachment hole at each main face.

11. A heater block for use in a modular chromatography column heating system comprising:

a solid body of a good heat conducting metal, the body having two opposite main faces, each main face having flat, coplanar reference surfaces, the reference surfaces of each main face being parallel to the reference surfaces of the opposite main face, the body also having side faces and end faces, at least two longitudinal channels for chromatography columns formed in each main face extending the length of the body between the end faces, wherein the channels in the opposite main faces have different widths.

12. The heater block of claim 11 wherein the channels in each main face are formed as half-cylindrical channels.

13. The heater block of claim 12 wherein two additional parallel channels for preheater tubes are formed in one of the main faces parallel to the other channels in the main face and extending the length of the heater block between the end faces, the two additional channels having a width smaller than the width of the half-cylindrical channels in the main face.

14. The heater block of claim 11 wherein the body of the heater block is formed of aluminum and including a corrosion resistant coating on the surfaces of the body.

15. The heater block of claim 11 wherein the end faces of the heater block are flat and parallel to each other, the channels in the main faces are formed perpendicular to the end faces, and including an attachment hole formed through the body between the main faces, and wherein the length of the heater block between the end faces is an even integer multiple of the distance between a center line of the attachment hole through the heater body and the most closely adjacent end face.

16. The heater block of claim 15 further including a counter bore wider than the attachment hole formed in the body about the attachment hole at each main face.

17. The heater block of claim 11 wherein the side faces of the heater block are parallel to each other and parallel to the channels in the main faces, wherein one of the main faces has two half-cylindrical channels formed therein of the same width and wherein such channels are parallel to and spaced an equal distance from the side faces.

18. The heater block of claim 11 wherein one of the main faces has two half-cylindrical channels formed therein which are about ¼ inch in width, the other main face has two half-cylindrical channels formed therein, one of which is about ½ inch in width and the other of which is about ⅜ inch in width.

19. The heater block of claim 18 wherein one of the main faces has two additional channels formed therein between the end faces to accommodate preheater tubes therein, each additional channel having a width of about 0.070 inch.

20. A modular chromatography column heating system comprising:
   a heater compartment for containing a chromatography column and a heater plate within the compartment;
   a set comprised of pairs of heater blocks, each heater block comprising:
      a solid body of a good heat conducting metal, the body having two opposite main faces, each main face having flat, coplanar reference surfaces, the reference surfaces of each main face being parallel to the reference surfaces of the opposite main face, the body also having side faces and end faces, at least one longitudinal channel for a chromatography column formed in each main face extending the length of the body between the end faces, wherein one of the main faces of each heater block has two half-cylindrical channels formed therein which are about ¼ inch in width, the other main face of each heater block has two half-cylindrical channels formed therein, one of which is about ½ inch in width and the other of which is about ⅜ inch in width; and
   means for holding the heater blocks in pairs to the heater plate with the adjacent main faces in each pair having channels therein aligned to define a channel for a chromatography column, and with the channels for a chromatography column in each pair of blocks aligned to define a channel through the set of pairs of blocks.

21. The chromatography column heating system of claim 20 wherein at least two channels are formed in each main face of each heater block that extend between the end faces parallel to each other.

22. The chromatography column heating system of claim 21 wherein two additional parallel longitudinal channels for preheater tubes are formed in one of the main faces of each heater block parallel to the other channels in the main face and extending the length of the heater block between the end faces, the two additional channels having a width smaller than the width of the half-cylindrical channels in the main face.

23. The chromatography column heating system of claim 20 wherein the body of each heater block is formed of aluminum and including a corrosion resistant coating on the surfaces of the body.

24. The chromatography column heating system of claim 20 wherein the side faces of each heater block are parallel to each other and parallel to the channels formed in the main faces of each heater block, wherein one of the main faces of each heater block has two half-cylindrical channels formed therein of the same width and wherein such channels are parallel to and spaced an equal distance from the side faces.

25. The chromatography column heating system of claim 20 wherein one of the main faces of each heater block has two additional channels formed therein between the end faces to accommodate preheater tubes therein, each additional channel having a width of about 0.070 inch.

26. The chromatography column heating system of claim 20 wherein the means for holding the pairs of heater blocks on the heater plate includes an attachment hole formed in each of the heater blocks extending between the main faces of the blocks, a series of spaced threaded holes in the heater plate, the attachment holes in each block spaced from the end faces so that the attachment holes in each pair of blocks align with each other and with the threaded holes in the heater plate when the blocks are placed together in position with abutting end faces, and attachment screws passed through the aligned holes in the heater blocks in each pair and into one of the threaded holes in the heater plate into which the screw is turned to hold the pairs of heater blocks together onto the heater plate.

27. The chromatography column heating system of claim 26 wherein the threaded holes in the heater plate are in standoffs mounted in and extending up from the heater plates and including a counter bore that is wider than the attachment hole formed in the body of each block about the attachment hole formed in the body of each block about the attachment hole at each main face.

28. The chromatography column heating system of claim 20 wherein the end faces of each heater block are flat and parallel to each other, and the channels in the main faces of each heater block are formed perpendicular to the end faces, and wherein the length of the heater blocks between the end faces is an even integer multiple of the distance between the center line of the attachment hole through the heater block body and the most closely adjacent end face.

29. The chromatography column heating system of claim 20 wherein the set of pairs of heater blocks includes at least two pairs of heater blocks having different lengths between the end faces of the blocks whereby the number of heater blocks in adjacent end face to end face relationship may be selected by the operator to match the length of a chromatography column.

30. The chromatography column heating system of claim 29 wherein the set of heater blocks includes at least one pair of blocks having a length of 4 inches and one pair of blocks having a length of 2 inches.

* * * * *